(12) United States Patent
Wang

(10) Patent No.: US 11,246,554 B2
(45) Date of Patent: Feb. 15, 2022

(54) SMART GRID PROCESSING ENABLED BY AEC RECONFIGURATION

(71) Applicant: CARESTREAM HEALTH, INC., Rochester, NY (US)

(72) Inventor: Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 34 days.

(21) Appl. No.: 16/716,629

(22) Filed: Dec. 17, 2019

(65) Prior Publication Data

US 2021/0177369 A1 Jun. 17, 2021

(51) Int. Cl.
*A61B 6/00* (2006.01)

(52) U.S. Cl.
CPC ............... *A61B 6/542* (2013.01); *A61B 6/42* (2013.01); *A61B 6/5282* (2013.01)

(58) Field of Classification Search
CPC .......... A61B 6/542; A61B 6/5282; A61B 6/42
USPC ......................................................... 378/97
See application file for complete search history.

(56) References Cited

U.S. PATENT DOCUMENTS

| 7,632,016 B1* | 12/2009 | Huang .................. A61B 6/542 378/207 |
| 8,873,712 B2 | 10/2014 | Wang et al. |
| 2004/0096035 A1 | 5/2004 | Yamazaki et al. |
| 2011/0249791 A1* | 10/2011 | Wang .................... A61B 6/547 378/62 |
| 2011/0249799 A1* | 10/2011 | Lalena ................ A61B 6/4266 378/97 |
| 2015/0342554 A1 | 12/2015 | Mentrup et al. |

OTHER PUBLICATIONS

Barski et al., "Image Quality Impact of SmartGrid Processing in Bedside Chest Imaging," Retrieved from Internet, Oct. 1, 2017, 5 pages.
International Search Report dated Mar. 25, 2021 for International Application No. PCT/US202/062769, 3 pages.

* cited by examiner

*Primary Examiner* — David P Porta
*Assistant Examiner* — Gisselle M Gutierrez

(57) ABSTRACT

A radiographic imaging system uses an automatic exposure control device configured at a default shut-off threshold. If the radiographic imaging system includes a processor programmed to process the image by executing a scatter removal algorithm thereupon, the shut-off threshold of the AEC is increased prior to capturing the radiographic image.

9 Claims, 6 Drawing Sheets

SMART GRID PROCESSING ENABLED BY AEC RECONFIGURATION

CROSS REFERENCE TO RELATED APPLICATIONS

This application is related in certain respects to U.S. Pat. No. 8,873,712, issued Oct. 28, 1014, in the name of Wang et al., and entitled EXPOSURE CONTROL USING DIGITAL RADIOGRAPHY DETECTOR, which is hereby incorporated by reference as if fully set forth herein in its entirety.

BACKGROUND OF THE INVENTION

The subject matter disclosed herein relates to radiographic imaging systems, in particular, to radiographic imaging systems using an automatic exposure control (AEC) device.

Scattered radiation is known to degrade image quality in diagnostic x-ray imaging. Traditional methods of reducing scatter include collimation, utilizing an air-gap, and/or utilizing an anti-scatter grid. Best practices in radiography prescribe collimation on every exam and, while this is helpful, it is not completely sufficient due to scatter that occurs within the subject. Likewise, air-gap techniques are helpful, but are not practical at the bedside. Anti-scatter grids are the most popular means of reducing x-ray scatter in portable imaging, but they present challenges to radiographers such as positioning and alignment. Image processing tools, such as SmartGrid from Carestream Health, Inc., have been developed to compensate for the effects of x-ray scatter in a radiographic image, and produces results comparable to those of a physical anti-scatter grid. The SmartGrid algorithm estimates the scatter distribution and removes it from the radiographic image, resulting in an image with improved contrast. Many physical factors affect scatter: the energy spectrum of the x-ray beam, thickness and material composition of the subject being imaged, and collimation, for example. The SmartGrid algorithm accommodates these variables automatically and so its use results in image quality that approximates anti-scatter grid visual performance.

A scatter removal algorithm is an enhancement algorithm that improves radiographic image contrast by suppressing scatter in the image. The fundamental method includes developing a scatter distribution image, which is a representation of the scatter contained in the radiographic image, and then subtracting it from the original input image. The scatter distribution image is developed using information from the image in both linear exposure space as well as attenuation space, which is a log transformation of the linear data. Segmentation is done to focus the development of the scatter field on relevant anatomical data and is used to compute the mean linear exposure of the input image. Parameters used to estimate scatter are determined. These include the scatter-to-primary ratio (SPR) and a curvature parameter used to control perturbation of the scatter distribution as the scatter field is developed. The scatter distribution image is computed based upon the default assumption that every object exposed by x-rays has a basic (default) scatter distribution that is characterized by a certain level of energy and scatter intensity variation across the whole object field of view. Adaptive updating of the scatter intensity across the entire object field of view is performed in a repetitive fashion based upon the SPR parameter for a prescribed number of iterations.

The discussion above is merely provided for general background information and is not intended to be used as an aid in determining the scope of the claimed subject matter.

BRIEF DESCRIPTION OF THE INVENTION

Scatter removal processing has demonstrated that equivalent radiographic image quality can be achieved without using an anti-scatter grid at a dose level comparable to that when an anti-scatter grid is used. Compensating the anti-scatter grid bucky factor can be easily performed with portable imaging where the exposure level is determined manually by the operator. However, for a radiographic system with AEC, the exposure level of the detector to the x-ray beam is preconfigured generically by programming an AEC trigger level. When a radiographic image is captured without an anti-scatter grid the AEC will be triggered more quickly, as compared to the same exposure with an anti-scatter grid, at a lower x-ray exposure level to the subject. This automatically applied lower exposure level to the subject does not allow a scatter removal algorithm to fully realize its benefit. To overcome this issue, whenever a scatter removal algorithm is to be used, either without a grid or with a low ratio grid, the AEC will be preconfigured at a higher trigger level to ensure enough primary exposure is delivered to the subject as if a high ratio grid is used in the x-ray beam path.

A radiographic imaging system uses an automatic exposure control device configured at a default shut-off threshold. If the radiographic imaging system includes a processor programmed to process the image by executing a scatter removal algorithm thereupon, the shut-off threshold of the AEC is increased prior to capturing the radiographic image.

In one embodiment, a radiographic imaging system includes an x-ray source, an x-ray detector, and an automatic exposure control (AEC) device coupled to the x-ray source. The AEC is configured to trigger a shutdown of the x-ray source when the AEC receives an amount of x-ray energy that satisfies a preset threshold. A processing system may receive a request to execute a program for removing x-ray scatter in the captured radiographic image and, in response, the processing system increases the preset threshold for triggering the AEC.

In another embodiment, a method of capturing and processing a radiographic image of a subject includes positioning an x-ray source and an x-ray detector about a subject to be radiographically imaged. A default threshold is preset in an AEC device configured to terminate x-ray emission from the x-ray source. In response to a request for using a scatter removal algorithm, the preset default threshold of the AEC is increased prior to capturing the radiographic image of the subject.

In another embodiment, a method of using an AEC in a radiographic imaging system includes providing an AEC having a programmed default shut-off threshold. After determining that the radiographic imaging system is configured to process images captured by the radiographic imaging system to remove scatter radiation effects, the shut-off threshold of the AEC is increased prior to capturing the radiographic image of the subject.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
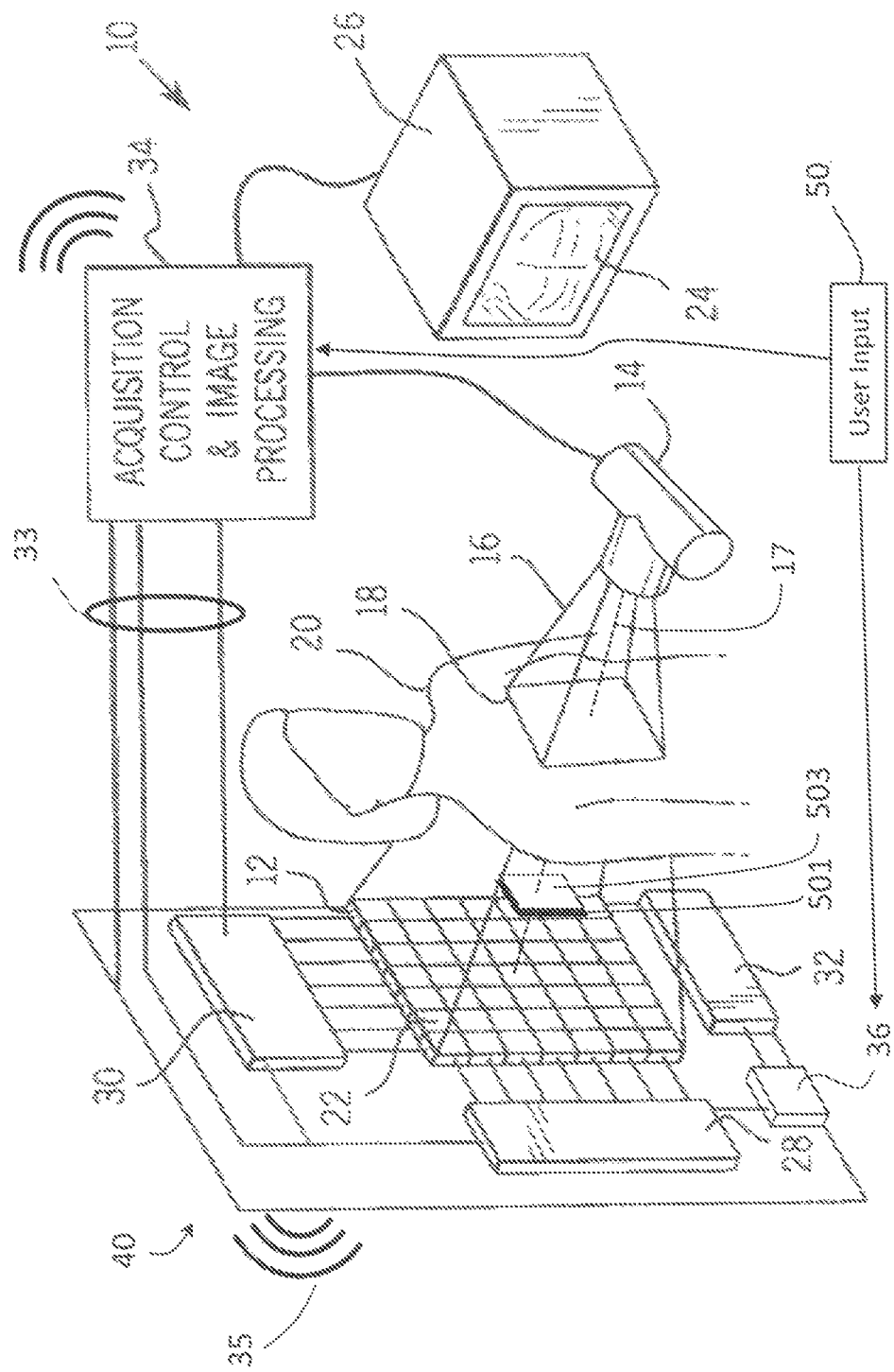
FIG. 1 is a schematic perspective view of an exemplary x-ray imaging system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photo sensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human subject in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing system 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing system 34 over a connected cable 33 (wired), or the DR detector 40 and the acquisition control and image processing system 34 may be equipped with a wireless transmitter and receiver to transmit radiographic image data wirelessly 35 to the acquisition control and image processing system 34. The acquisition control and image processing system 34 may include a processor and electronic memory (not shown) to control operations of the DR detector 40 as described herein, including control of circuits 28, 30, and 32, for example, by use of programmed instructions, and to store and process image data. The acquisition control and image processing system 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing system 34 functions may reside in the detector 40 in an on-board processing system 36 which may include a processor and electronic memory to control operations of the DR detector 40 as described herein, including control of circuits 28, 30, and 32, by use of programmed instructions, and to store and process image data similar to the functions of standalone acquisition control and image processing system 34. The image processing system may perform image acquisition and image disposition functions as described herein. The image processing system 36 may control image transmission and image processing and image correction on board the detector 40 based on instructions or other commands transmitted from the acquisition control and image processing system 34, and transmit corrected digital image data therefrom. Alternatively, acquisition control and image processing system 34 may receive raw image data from the detector 40 and process the image data and store it, or it may store raw unprocessed image data in local memory, or in remotely accessible memory. A user input 50 may include input devices such as a keyboard, a mouse, a touchscreen, or other input devices configured to allow an operator to set or request specific parameters to be used by either of the processing systems 34, 36, for controlling operations, such as exposure levels, AEC trigger levels and duration, of the digital radiographic (DR) imaging system 10.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components. An automatic exposure control (AEC) device 501 may be positioned between the subject 20 and the DR detector 40 in the path of the x-ray beam 16. An anti-scatter grid 503 may be positioned between the subject 20 and the AEC device 501 in the path of the x-ray beam 16. The AEC device 501 and the anti-scatter grid 503 are represented in FIG. 1 in a miniaturized form for clarity of illustration. A full size AEC device 501 and anti-scatter grid 503 may be positioned in the planes occupied by the AEC device 501 and the anti-scatter grid 503 represented in FIG. 1. The full size AEC device 501 and anti-scatter grid 503 may be formed having a size approximately equivalent in area to the DR detector 40, and are described in more detail herein in relation to FIG. 5. The AEC device 501 may be communicatively connected to the processing systems 34, 36, in a similar fashion as the detector 40, as described herein, for transmitting an x-ray source termination signal to, and for receiving an instruction to set a variable AEC trigger level from, the processing system 34, 36.

Figure 2:
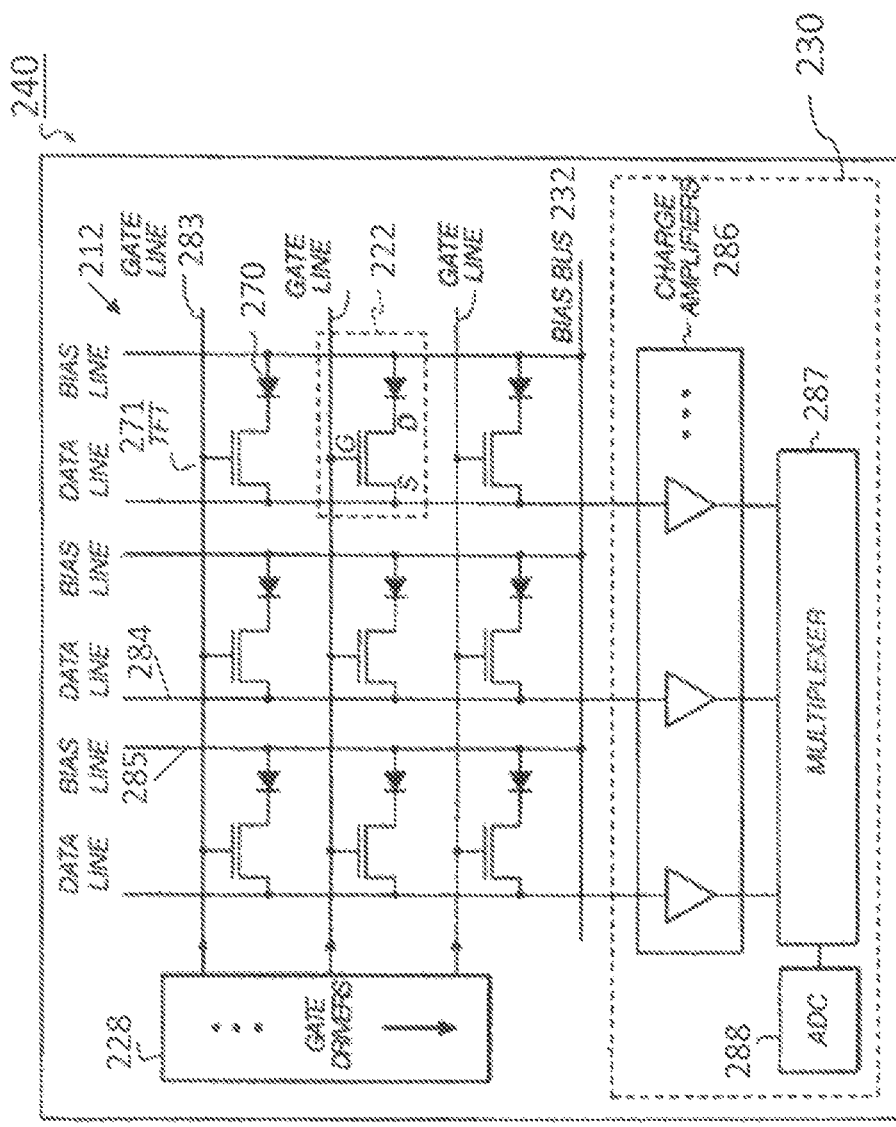
FIG. 2 is a schematic diagram of a photosensor array in a radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
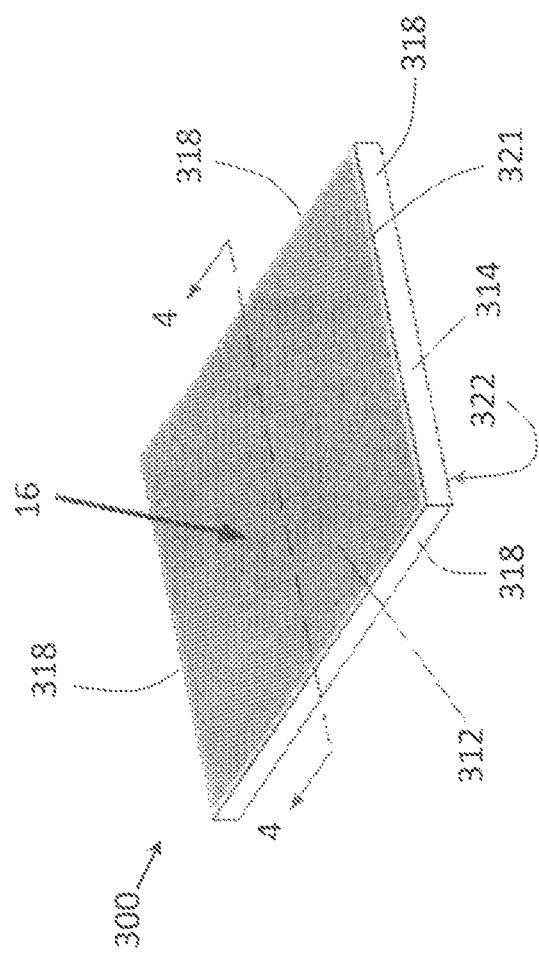
FIG. 3 is a perspective diagram of an exemplary DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
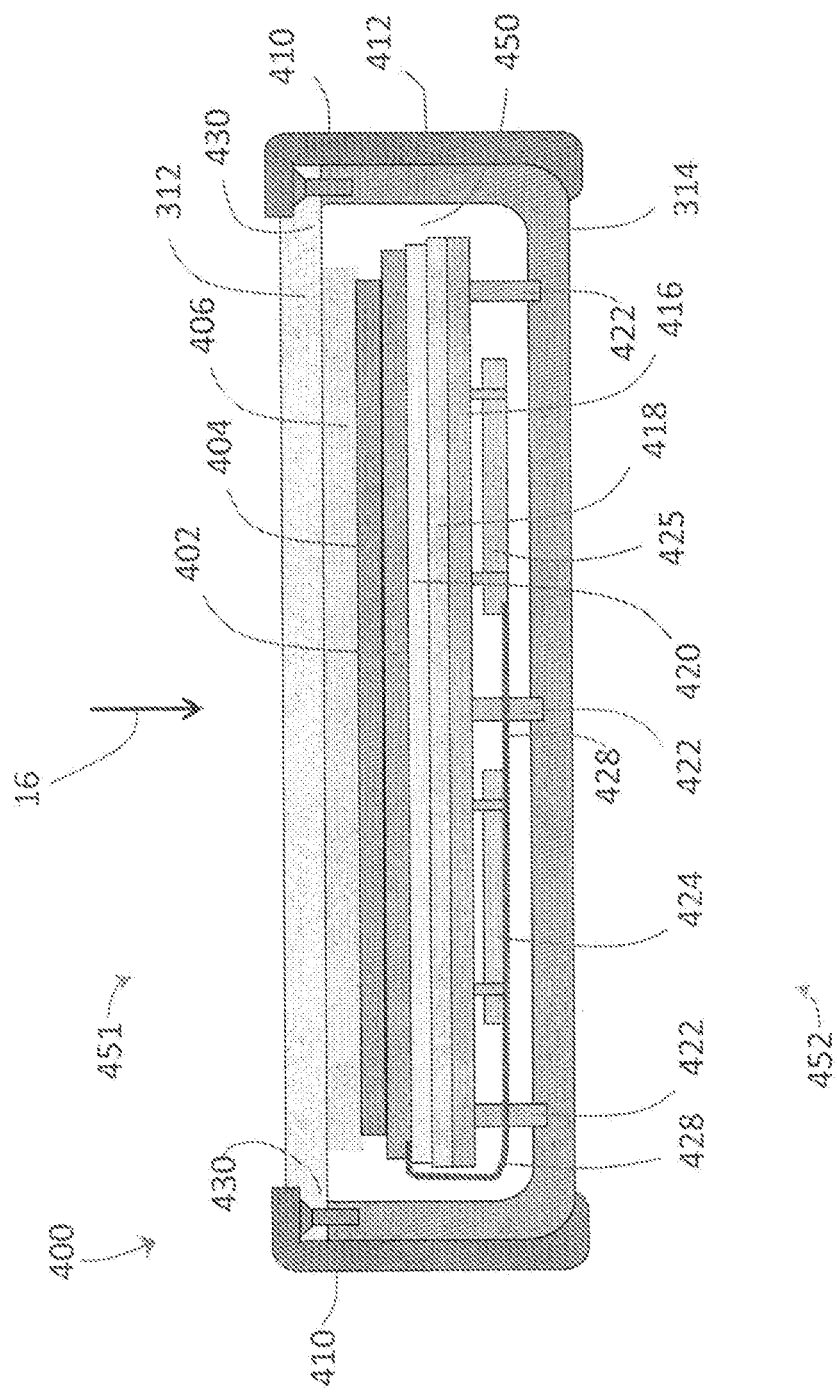
FIG. 4 is a cross section diagram of an exemplary DR detector.

With reference to FIG. 4, there is illustrated in schematic form an exemplary cross-section view along section 4-4 of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer, in one embodiment, or flexible substrate comprising polyimide or carbon fiber upon which the array of photosensors 402 may be formed to allow adjustable curvature of the array, and may comprise another layer of the multilayer structure. Under the substrate layer 420 a radio-opaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, the bias circuit 32, and processing system 36 (all of FIG. 1) may be formed adjacent the imaging array 402 or, as shown, may be disposed below frame support member 416 in the form of integrated circuits (ICs) electrically connected to printed circuit boards 424, 425. The imaging array 402 may be electrically connected to the readout electronics 424 (ICs) over a flexible connector 428 which may comprise a plurality of flexible, sealed conductors known as chip-on-film (COF) connectors.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
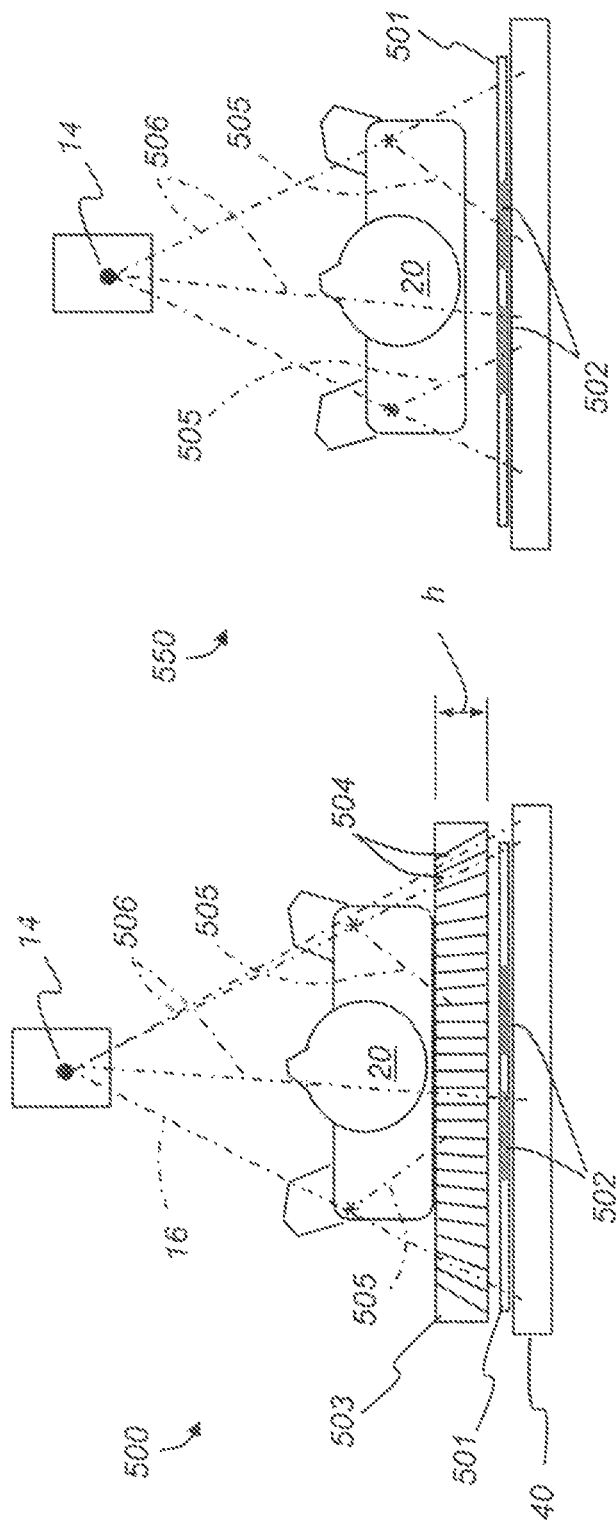
FIG. 5A is a schematic view showing components of an exemplary x-ray imaging system that uses an anti-scatter grid and an automatic exposure control device.
FIG. 5B is a schematic view showing components of the exemplary x-ray imaging system of FIG. 5A, but without an anti-scatter grid.

FIG. 5A is a schematic diagram of a radiographic imaging system 500 having an x-ray source 14, a DR detector 40, an AEC device 501 having x-ray energy sensor elements 502, and an anti-scatter grid 503 wherein channels 504 extend through the anti-scatter grid 503 each having a central linear axis that altogether converge toward a focal point shown as x-ray source 14. The position of a subject 20 relative to the x-ray system 500 is also shown in FIG. 5. As described in U.S. Pat. No. 8,873,712, the AEC device 501 measures an amount of x-ray energy accumulating in the x-ray energy sensor elements 502 as emitted by x-ray source 14, which x-ray energy travels through the subject 20 and impacts the x-ray energy sensor elements 502. The AEC device 501 may include a variable programmable threshold configured so that it transmits a shut-off, or termination, signal to turn-off the x-ray source 14 when the amount of x-ray energy accumulating in the x-ray energy sensor elements 502 reaches the variable programmable threshold.

The channels 504 that extend through the anti-scatter grid 503 may be formed to have a different focal length than the one illustrated, i.e., they may converge toward a point further or closer than the x-ray source 14 as illustrated. The channels 504 are separated by thin strips of lead having sufficient thickness to absorb scattered x-rays 505. A grid ratio for anti-scatter grid 503 may be defined as a height, or thickness, h of the anti-scatter grid 503 divided by a distance separating the lead strips. The channels 504 may be filled with aluminum or an aluminum alloy to maintain their shape and alignment toward a desired focal point. The x-rays 506 of x-ray beam 16 emitted by the x-ray source 14 may be said to substantially coincide with the central linear axes of channels 504 such that they pass through the channels 504 of the anti-scatter grid 503 to the DR detector 40 along a linear trajectory. These x-rays 506 may be referred to a primary x-rays because they pass directly through the subject 20, through the channels 504, and then are captured by the DR detector 40 after travelling in a substantially linear path from the x-ray source 14. The x-rays 506 may also pass through AEC device 501 and its x-ray energy sensor elements 502 depending on where the AEC device 501 is positioned. The primary x-rays 506 may be defined in relation to scattered x-rays 505 that impact a portion of the subject 20 and are deflected from their original linear trajectories in directions that are not substantially aligned with a central axis of a channel 504 and so are absorbed by the lead strips which form the sidewalls of the channels 504. While not shown in FIG. 5 for clarity of illustration, the radiographic imaging system 500 may be configured to include the image processing systems 34 and/or 36 as illustrated in the digital radiographic (DR) imaging system 10 of FIG. 1, including wired and/or wireless communication between the processing systems 34, 36, the x-ray source 14, the detector 40 and the AEC device 501.

FIG. 5B is a schematic diagram of a radiographic imaging system 550 similar to that shown in FIG. 5A but without the anti-scatter grid 503. Without the anti-scatter grid 503 both primary x-rays 506 and scattered x-rays 505 reach the DR detector 40. The scattered x-rays 505 cause image noise and blurring in the radiographic images captured by the DR detector 40. Because the x-ray energy sensor elements 502 of the AEC device 501 do not distinguish between primary x-rays 506 and scattered x-rays 505 impacting these sensor elements, the x-ray energy sensor elements 502 will accumulate x-ray energy at a faster rate when a subject 20 is radiographically imaged without use of an anti-scatter grid 503. Thus, the AEC device 501 will transmit a shut-off signal after a shorter duration of an x-ray exposure that does not include the anti-scatter grid 503. When an anti-scatter grid 503 is used during an x-ray exposure a higher proportion of primary x-rays will reach the DR detector 40 because a portion of scattered x-rays 505 will be absorbed by the anti-scatter grid 503. Because a portion of the scattered-x-rays 505 will be blocked by the anti-scatter grid 503 the rate of accumulation of x-ray energy in the AEC device 501 will be lower, so the AEC device 501 will transmit a shut-off signal after a longer duration of the x-ray exposure as compared with the exposure that does not use an anti-scatter grid 503. Thus, a radiographic image capture by the DR detector 40 is clearer and less blurry when an anti-scatter grid 503 is used because the proportion of captured primary x-ray energy relative to scattered x-ray energy is higher and so forms a radiographic image with less noise caused by scattered x-rays 505. The proportion of captured scattered x-rays relative to captured primary x-rays in a radiographic image may be referred to as a scatter-to-primary ratio (SPR).

When an anti-scatter grid 503 is used to capture a radiographic image of a subject 20 in a radiographic imaging system 500 having an AEC device 501, the presence of the anti-scatter grid 503 inherently increases the duration of an exposure to x-ray source 14, because less of the x-ray energy emitted by x-ray source 14 reaches the AEC device 501. This increases the amount, and proportion relative to scattered x-rays 505, of primary x-rays 506 captured by the DR detector 40, which provides a radiographic image of the subject 20 having higher diagnostic quality, such as better contrast, than a more blurry radiographic image of the subject 20 captured without use of the anti-scatter grid 503.

With respect to using a scatter removal algorithm to process captured radiographic images of a subject 20, a radiographic imaging system 500, 550, and a method of operating such a system is disclosed herein. To improve radiographic image quality provided by processing a radiographic image using a scatter removal algorithm, the proportion of primary x-rays 506 captured by a DR detector 40 in such a radiographic image may be increased by raising an AEC trigger threshold to approximate the amount of increased primary x-ray energy that is provided to DR detector 40 when using an anti-scatter grid 503, as described herein. In one embodiment, a formula may be used to program a higher trigger level for the AEC device 501. For example, if a known default AEC trigger level t is used for a particular radiographic examination, then a formula such as T=(SPR+1)·t can be used to reset (increase) the trigger level of the AEC device 503 wherein T is the increased trigger level and SPR is the known scatter-to-primary ratio of x-rays in a radiographic image captured without use of an anti-scatter grid 503.

Figure 6:
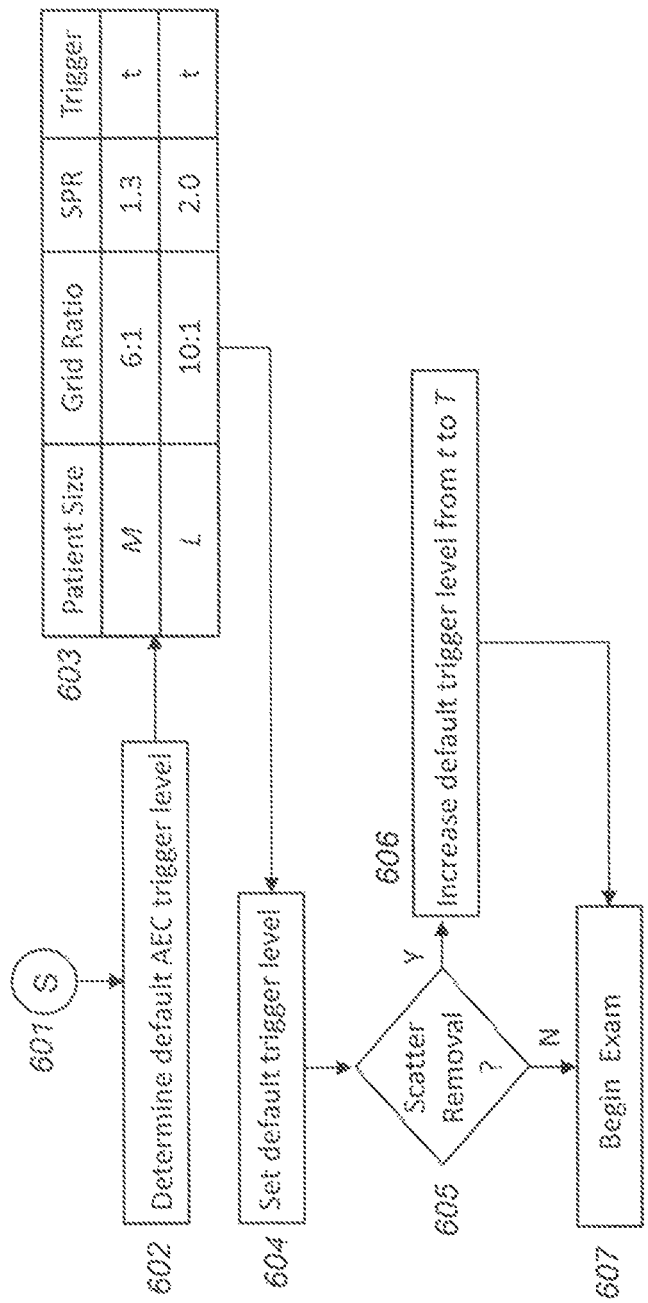
FIG. 6 is a flowchart of a method for operating a radiographic imaging system having an automatic exposure control device.

FIG. 6 is a flowchart of a method for operating a radiographic imaging system 500, 550, and an AEC device 501 used therein. The method starts 601 with determining a default trigger level, at step 602, for the AEC device 501. This may involve an operator identifying and inputting into the imaging system 500, 550, a size of a subject to be radiographically imaged, such as small, medium M, or large L. The radiographic imaging system 500, 550, may be programmed to receive the operator input and automatically set a default trigger level t of the AEC device 501, at step 603, using known parameters of the radiographic imaging system 500, 550, when examining subjects having a particular size. A table, as shown in FIG. 6 for step 603, may be stored in the processing system 34, 36, of the radiographic imaging system 500, 550, corresponding to the operator input patient size which identifies, and thereafter is used by, the processing system 34, 36, to set, at step 604, a determined trigger level t in the AEC 501. If the operator then inputs an instruction, or data, to the radiographic imaging system, at step 605, that a scatter removal algorithm will not be used because, for example, the operator intends to use an anti-scatter grid 503, the radiographic imaging system 500, 550, may then initiate a standard procedure for beginning a radiographic examination at step 607. If the operator inputs to the processing system 34, 36, of the radiographic imaging system 500, 550, at step 605, that a scatter removal algorithm will be used to process a radiographic image captured by the radiographic imaging system 500, 550, because the operator does not intend to use an anti-scatter grid 503 or intends to use an anti-scatter grid having a very low grid ratio, the radiographic imaging system may then execute a program for resetting the trigger level of the AEC device, at step 606, using a formula corresponding to the operator entered size of the subject to be imaged. The radiographic imaging system may use the determined default trigger level t from step 603 and increase it to a trigger level T using the formula T=(SPR+1)·t as described herein, wherein the value SPR may be obtained from the table stored in the processing system 34, 36, corresponding to the operator input subject size. After resetting (increasing) the trigger level of the AEC device 501, at step 606, the radiographic imaging system 500, 550, then initiates a standard procedure for beginning a radiographic examination at step 607.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A radiographic imaging system comprising:
    an x-ray source;
    an x-ray detector;
    an automatic exposure control device coupled to the x-ray source and configured to trigger a shutdown of the x-ray source when the AEC receives an amount of x-ray energy that satisfies a preset threshold; and
    a processing system for controlling the x-ray source, the x-ray detector, and for processing a radiographic image captured by the detector, the processing system configured to receive a request to execute a program for reducing x-ray scatter in the captured radiographic image, wherein the processing system is configured to set a trigger level of the automatic exposure control device according to whether or not the program for reducing x-ray scatter was requested, wherein the processing system is configured to increase the preset threshold for triggering the AEC if the program for reducing x-ray scatter was requested.

2. The system of claim 1, wherein the system determines an amount to increase the preset threshold based on data indicating a size of a subject being imaged by the system.

3. The system of claim 1, wherein the processing system is further configured to set the threshold T according to the formula T=(s+1)×t, wherein s represents a scatter value of x-ray scatter energy received at the AEC device and t represents a default threshold of the AEC.

4. A method of capturing and processing a radiographic image of a subject, the method comprising the steps of:
   positioning an x-ray source and an x-ray detector about the subject to be radiographically imaged;
   setting a default threshold in an AEC device configured to terminate x-ray emission from the x-ray source in response to receiving an amount of x-ray energy corresponding to the default threshold;
   determining that a first algorithm will be used to process the radiographic image of the subject, the first algorithm configured to remove x-ray scatter noise from the captured radiographic image of the subject; and
   increasing the preset default threshold of the AEC in response to the step of determining, prior to capturing the radiographic image of the subject.

5. The method of claim 4, wherein the step of increasing the preset default threshold comprises calculating the increased preset threshold according to the formula T=(s+1)×1, wherein s represents an estimated scatter-to-primary ratio of the x-ray energy based on a size of the subject, and t represents a default threshold of the AEC.

6. A method of using an AEC in a radiographic imaging system, the method comprising:
   providing an AEC having a programmed default shut-off threshold;
   determining that the radiographic imaging system includes a processor configured to process a captured radiographic image captured by the radiographic imaging system to remove scatter radiation in the captured radiographic image;
   increasing a shut-off threshold of the AEC from the programmed default shut-off threshold prior to capturing the radiographic image of the subject.

7. The method of claim 6, wherein the step of increasing the shut-off threshold comprises calculating the increased shut-off threshold according to the formula T=(s+1)×t, wherein T represents the increased shut-off threshold, s represents an estimated scatter effect, and t represents the default shut-off threshold.

8. The method of claim 7, wherein the estimated scatter effect is based on a size of the subject.

9. The method of claim 7, wherein the estimated scatter effect is a value representing an estimated x-ray scatter energy to x-ray primary energy ratio.

* * * * *